US005285491A

United States Patent [19]

Muylle et al.

[11] Patent Number: 5,285,491

[45] Date of Patent: Feb. 8, 1994

[54] DENTAL FILM PACKET

[75] Inventors: Wilfried Muylle, Schoten; Guido Godden, Bornem, both of Belgium

[73] Assignee: Agfa-Gevaert N. V., Mortsel, Belgium

[21] Appl. No.: 27,793

[22] Filed: Mar. 8, 1993

[30] Foreign Application Priority Data

Apr. 1, 1992 [EP] European Pat. Off. ........... 92200924

[51] Int. Cl.[5] ........ A61B 6/14

[52] U.S. Cl. ........ 378/168; 378/169; 378/173

[58] Field of Search ........ 378/166, 167, 168, 169, 378/173, 174; D6/528, 534

[56] References Cited

U.S. PATENT DOCUMENTS

T903,035 9/1971 Opperman ........ 378/167

*Primary Examiner*—David P. Porta
*Assistant Examiner*—Don Wong
*Attorney, Agent, or Firm*—William J. Daniel

[57] ABSTRACT

A dental film packet, comprises a film pack in a sealed envelope for intra-oral use for dental X-ray purposes. The envelope consists of a pair of thin pockets 21 and 22 of injection moulded plastics material, mating by means of tongues and cut-outs which may be held together and sealed by a band of adhesive tape. The envelope 20 has edges 29, 30 and corners 31 which are smoothly rounded so that the envelope 20 is devoid of any sharp edges. It will therefore generally cause the patient considerably less discomfort than the conventional form of packet.

6 Claims, 1 Drawing Sheet

FIG. 1
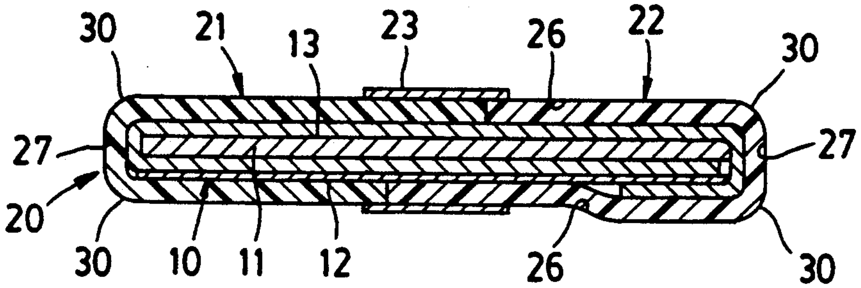
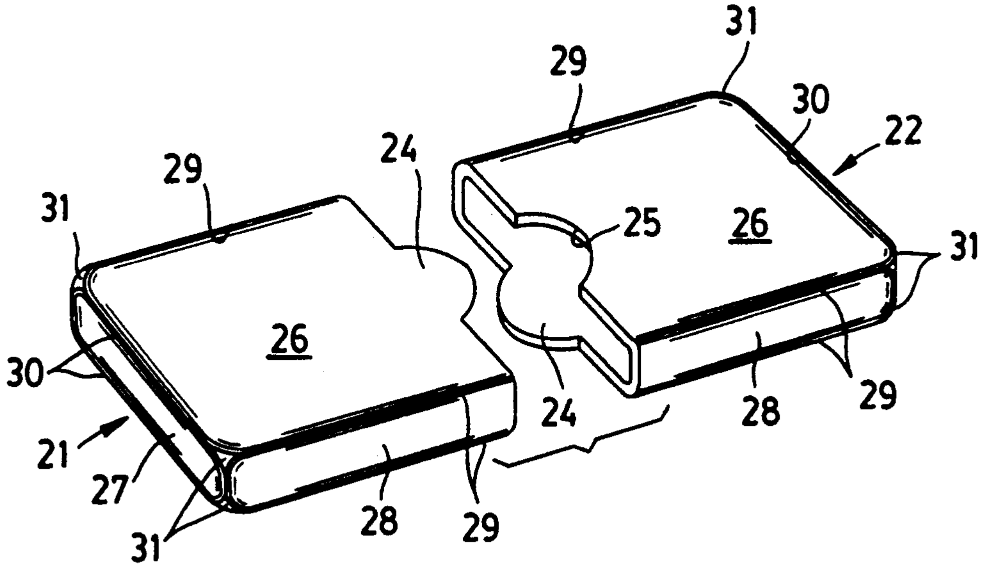
FIG. 2

DENTAL FILM PACKET

FIELD OF THE INVENTION

The present invention relates to dental film packets, that is, to packets which comprise an X-ray film pack contained in a sealed envelope for intra-oral use for dental purposes.

BACKGROUND OF THE INVENTION

Dental film packets are widely used for X-raying teeth. The usual form of such a packet is a sealed (i.e. waterproof) packet containing layers of X-ray sensitive film, metal foil, and black paper. The packet is held in place in the patient's mouth while the X-ray is being taken, and is then removed and the film is taken out and developed. The film obviously then shows the desired X-ray; two films are sometimes used, automatically giving two copies of the X-ray picture. The metal foil serves to absorb the X-rays after they have passed through the film, so reducing the total X-ray dosage to the patient. The black paper eases the handling of the film when it is being taken out of the packet tg be developed.

Various forms of envelopes are known for providing the outer sealing of the packet. The usual current form is made of plastics material, typically polyvinyl chloride, and is produced by stamping. Two webs of the plastics material are interleaved with film packs and are fed through a machine in which the two webs are heat-sealed together around each film pack and the resulting packet is simultaneously separated from the webs and the other packets being formed. The manufacture of packets using such envelopes is readily automated and the resulting packets are inexpensive.

As stated above, the packets are intended for intra-oral use. The packet may be supported in a clip on the end of a rod, and held in position in the patient's mouth by the patient gripping the rod between his teeth, or it may simply be held in position by the patient's finger. The X-ray beam is directed from outside the mouth through the teeth and onto the packet.

Packets made in the manner outlined above tend to have somewhat hard and sharp edges due to the heat-sealing of the two layers of plastics material. This is a drawback, because such edges can cause discomfort to the patient, particularly if the patient has a sensitive lining to the mouth (as may easily be the case for someone requiring dental treatment).

Several proposals have involved providing a band of some sort around the periphery of the envelope, to act as a cushion around the envelope's hard and sharp edge; among such proposals are WO 90/02358 (Liese/Eastman Kodak) and U.S. Pat. No. 4,852,143 (Scheier at al), both of which contain references to other somewhat similar proposals. A packet having such a band will therefore not scratch the patient.

However, such bands have their own disadvantages.

Sometimes the band absorbs moisture and may therefore dry the patient's mouth and cause discomfort in that way, and if the band expands on being moistened, its expansion may easily cause displacement of the packet from its desired position and may even cause discomfort if the expansion is too great.

The automatic manufacture of such a packet is not easy, while manual manufacture is inconvenient, requires particular care to avoid possible contamination, and is expensive. If the band is not made integrally with the envelope, there will be a space along the inside of the band, between it and the envelope, which can be unhygienic, while making the band integrally with the envelope presents manufacturing difficulties and expense. The band can easily trap saliva and so make the exposed packet unpleasant to handle after use.

It has also been proposed, in U.S. Pat. No. 4,922,511 (Gay/Eastman Kodak), to provide a heat-sealed packet in which the envelope has an exceptionally wide margin around the central part containing the films. The idea is that this margin of the envelope will bend back on itself in use, so that the tissue of the patient's mouth will be contacted by the curved outer parts of the bends of the margins rather than by the hard edges of the packet.

This, however, increases the size of the packet, and this and the loss of rigidity makes it less convenient to handle, and in particular, it adds significantly to the size of a package, giving rise to inconveniences in bulk storage and supply of such film packets. Also, it may present inconveniences on being inserted into the patient's mouth. If the outer parts of the margin of the two layers of the plastics material used for the envelope are sealed together, then the rigidity of the margin will be substantial, and its width must be particularly great to achieve adequate flexibility, while if the sealing is confined to the inner parts of the margin, the two layers will form a loose crack at the outer parts of the margin which will tend to pick up moisture and so be unpleasant to handle and potentially unhygienic. Also, the folding or bending back of the margin is unlikely to be uniform around the whole of the edge of the packet, thereby producing kinks, and the larger size of the packet compared to a normal packet means that any potential for kinking is likely to be more serious.

DESCRIPTION OF THE INVENTION

Object of the Invention

The general object of the present invention is to provide an improved form of dental film packet in which at least some of the above disadvantages are alleviated.

Summary of the Invention

According to the present invention, there is provided a dental film packet comprising an X-ray film pack contained in a sealed envelope, characterized in that the envelope is formed of a pair of mating pockets formed by injection moulding and into each of which a part of the film pack is slid.

A dental film packet according to the invention may present a number of different advantages. The envelope may be made as thin as is consistent with the material of which it is made and the function which it has to perform and it may be a snug fit around the enclosed film pack, so it need not be unduly bulky, and it need not take up significantly more space than the usual form of heat-sealed film packet referred to above. Because the envelope is formed of a pair of mating pockets as defined, the line of the joint between those pockets will extend across the main faces of the packet rather than around its perimeter. Thus any discontinuity at the joint is less likely to cause discomfort to a patient. Furthermore, because the envelope is moulded, it may be given any desired external shape. Patient comfort is promoted if, as is preferred, said envelope has smoothly rounded edges and corners.

BRIEF DESCRIPTION OF THE DRAWINGS

A preferred embodiment of dental film packet according to the invention will now be described, by way of example, with reference to the accompanying drawings, in which:

FIG. 1 is a section through the packet; and

FIG. 2 is a perspective view of the envelope in exploded form.

DETAILED DESCRIPTION OF A PREFERRED EMBODIMENT OF THE INVENTION

Referring to FIG. 1, the packet comprises a film pack 10 in an envelope 20.

The film pack consists of an X-ray sensitive film 11, an X-ray opaque metal foil 12, and a sheet of black paper 13 wrapped round the film 11 as shown. The paper 13 helps to keep the film pack together and to protect the film 11 from light and scratches or other physical damage due to the metal foil 12 and the envelope 20 when the packet is disassembled after exposure by the envelope 20 being taken apart and the film pack 10 being taken out. (The film 11 would then be developed for inspection by the dentist.)

The envelope consists of two injection moulded pockets 21 and 22 into which the film pack is inserted and a strip of adhesive tape 23. The mutually facing open ends of the pockets abut against each other and are preferably held in this mated position by a strip of adhesive tape 23 which is wound round the waist of the packet. Such tape is preferably opaque to light. The mated pockets enclose a thin volume which is large enough to contain the film pack 10 as a snug fit, that is, with little or no free space. The film pack is shown with a clearance around it only for clarity of drawing; in practice, the film pack will usually fit reasonably tightly in the pockets.

As shown in the drawings, each pocket 21, 22 encloses approximately half of the length of the film pack 10. Since the packet is elongated, this give a shorter meeting line or joint between the two pocket end than does a possible alternative configuration in which each pocket encloses half of the width of the film pack.

The film pack is shown as having a slightly greater thickness towards one end, arising from the fact that the last portion or end flap of the paper 13 extends only partly along the length of the pack. This is because the thicknesses of the various layers have been exaggerated in the drawing for the sake of clarity. The pocket 22 is drawn shaped to accommodate this thickening. The metal foil 12 may be embossed with a raised pattern to give the film pack greater compressibility and so ease its insertion into the pockets 21, 22.

As shown in FIG. 2, the two pockets 21 and 22 are of closely similar shapes. Each has a tongue 24 on one side and a corresponding cut-out 25 on the other.

When the packet is being assembled by sliding the pockets over the two ends of the film pack, the film pack itself can act as a guide determining the alignment of each pocket relative to the other vertically (as seen in FIG. 2). The tongue 24 of each pocket engages in the cut-out 25 of the other, thereby determining the alignment of each pocket relative to the other laterally (as seen in FIG. 2). The relative alignment of the two pockets is thus completely determined.

A suitable length of the tape 23 is then wrapped around the two pockets where they meet, to complete the assembly. The width of the tape may be somewhat more than the combined length of the two tongues 24 in order to ensure light-tightness. The leading edge of the tape may be formed as a strip leader.

If desired, the mating portions of the pockets may be made more elaborate, to provide more accurate mating and/or self-centering alignment.

The pockets are made by injection moulding. The two pockets are shown in FIG. 1 as being of slightly different shapes, to match the illustrated contours of the film pack. This is by no means essential. The two pockets could be made as identical mouldings. However, it is preferred that the two pockets be moulded differently, in order to allow the front and back of the packet to be distinguished. This distinction can be enhanced by providing suitable embossment on the surfaces of the pockets. Such distinction could for example be provided by moulding some form of marking indicia into one face of one or both of the pockets 21, 22. Such marking could include one or more of the following: a manufacturer's Trade Mark, an indication of the speed of the film contained within the packet, a film batch number, an indication identifying the back, or indeed the front, of the packet and an indication of the number of films contained within the packet. (It is sometimes preferred that a film pack include two X-ray film plates in order that a copy may be sent to the patient's health insurer, whether this be a private insurance company or a government department.) Alternatively, the tape 23 could have identifying information printed on it, to identify the characteristics of the film pack and/or the front and back of the packet.

The pockets can conveniently be made of plastics materials such as polyethylene or polyurethane. These materials are chlorine-free, in contrast to the conventional polyvinyl chloride used for the standard form of packet discussed above. Thermosetting plastics material can also, of course be used for the present packets.

As will be apparent from the drawing, the envelope 20 is generally rectanguloid in shape having a pair of opposed major faces 26, a pair of opposed end faces 27 and a pair of side faces 28. The side faces 28 meet the major faces 26 at side edges 29 and the end faces 27 meet the major faces 26 at end edges 30. The envelope has four corners 31. As will be seen in the drawings, the envelope 20 has edges 29, 30 and corners 31 which are smoothly rounded so that the envelope 20 is devoid of any sharp edges. It will therefore generally cause the patient considerably less discomfort than the conventional form of packet. The rounding of the edges 29, 30 may be such as to leave distinct, generally flat side and end faces 28, 27, or it may be such that the sides and ends of the envelope are semi-circular or semi-elliptical in cross-section.

Further, the manner in which the conventional envelope is sealed results in it having a protruding margin. The present envelope does not require such a margin, and it can therefore be slightly smaller. This reduces patient discomfort and makes it easier to use, store and transport.

We claim:

1. A dental film packet comprising an X-ray film pack (10) contained in a sealed envelope (20), characterized in that the envelope is formed of a pair of mating pockets (21, 22) formed by injection moulding and into each of which a part of the film pack (10) is inserted.

2. A dental film packet according to claim 1, wherein said envelope (20) has smoothly rounded edges (29, 30) and corners (31).

3. A dental film packet according to claim 1, wherein each said pocket (21, 22) contains a part of the length of the film pack (10).

4. A dental film packet according to claim 1, wherein the pockets are held together by a band (23) of adhesive tape.

5. A dental film packet according to claim 1, wherein each pocket has a tongue (24) and a cut-out (25) mating with the tongue of the other pocket.

6. A dental film packet according to claim 1, wherein the pockets are made of chlorine-free plastics material.

* * * * *